United States Patent [19]
Ekenberg et al.

[11] Patent Number: 5,646,263
[45] Date of Patent: Jul. 8, 1997

[54] HIGH EFFICIENCY METHOD FOR ISOLATING TARGET SUBSTANCES USING A MULTISAMPLE SEPARATION DEVICE

[75] Inventors: Steven J. Ekenberg, Mt. Horeb; Paula R. G. Brisco, Madison, both of Wis.; Anne Louise Oaklander, Baltimore, Md.

[73] Assignees: Promega Corporation, Madison, Wis.; The Johns Hopkins University, Baltimore, Md.

[21] Appl. No.: 308,819

[22] Filed: Sep. 19, 1994

[51] Int. Cl.$^6$ .............................. C07H 1/06; C07H 21/00
[52] U.S. Cl. ............................................. 536/25.4; 435/7.1
[58] Field of Search ............................. 536/25.4; 435/7.1

[56] References Cited

U.S. PATENT DOCUMENTS

| | | | |
|---|---|---|---|
| 3,700,555 | 10/1972 | Widmark et al. | 435/2 |
| 3,970,518 | 7/1976 | Giaever | 435/234 |
| 4,018,886 | 4/1977 | Giaever | 436/526 |
| 4,230,685 | 10/1980 | Senyei et al. | 436/526 |
| 4,267,234 | 5/1981 | Rembaum | 427/127 |
| 4,375,407 | 3/1983 | Kronick | 435/29 |
| 4,452,773 | 6/1984 | Molday | 424/1.37 |
| 4,508,625 | 4/1985 | Graham | 210/695 |
| 4,554,088 | 11/1985 | Whitehead et al. | 252/62.54 |
| 4,659,678 | 4/1987 | Forrest et al. | 436/512 |
| 4,710,472 | 12/1987 | Saur et al. | 435/287 |
| 4,738,773 | 4/1988 | Müller-Ruchholtz et al. | 123/694 |
| 4,978,610 | 12/1990 | Forrest et al. | 204/153.12 |
| 4,988,618 | 1/1991 | Li et al. | 435/6 |
| 5,186,827 | 2/1993 | Liberti et al. | 210/222 |
| 5,200,084 | 4/1993 | Liberti et al. | 210/695 |

FOREIGN PATENT DOCUMENTS

| | | |
|---|---|---|
| 0 317 286 A2 | 5/1989 | European Pat. Off. . |
| WO90/10716 | 9/1990 | WIPO . |

OTHER PUBLICATIONS

R. R. Oder, *IEEE Trans. Magnetics*, 12 (1976) 428–435.
C. Owen and P. Liberti, *Cell Separation: Methods and Selected Applications*, vol. 4, Pretlow and Pretlow eds., Academic Press, New York (1987), pp. 254–275.
*Immunoassays for Clinical Chemistry*, pp. 147–162, Hunter et al., eds., Churchill Livingston, Edinborough (1983), pp. 147–162.
L. S. Hersh and S. Yaverbaum, *Clin. Chim. Acta*, "Magnetic Solid–Phase Radioimmunoassay," 63, pp. 69–72 (1975).
J. T. Kemshead and J. Ugelstad, *Molecular and Cellular Biochemistry*, "Magnetic separation techniques: their application to medicine," 67, pp. 11–18 (1985).
Product Information Sheet, Magnetic Particle Concentrator, DYNAL MPC 1, Product No. 12001, DYNAL, A.S., Oslo, Norway, 1991.
Product Information Sheet, BioMag Separators, Product Nos. 4101S, 4102S, and 4106S, Advanced Magnetics, Inc., Cambridge, Massachusetts (Received in 1991).
Product Information Sheet, Magic™, magnetic immunochemistry method, Corning (No Available Date).

*Primary Examiner*—Gary L. Kunz
*Attorney, Agent, or Firm*—Grady J. Frenchick; Stroud, Stroud, Willink, Thompson & Howard

[57] ABSTRACT

Methods for separating target particles, from a test medium in which the particles are suspended. The method contemplates utilization of blocking or masking particles which block or mask unwanted biological debris which tends to interfere with formation of complexes by which the target particles can be isolated. After centrifugation, the masking particles create a barrier between unwanted debris and test medium containing the target particles which permits the particles to be manipulated or modified without removing them from the debris. In a preferred aspect, magnetic separation techniques are used. In this aspect, non-magnetic 0.04 micron carboxylated polystyrene blocking particles are employed.

23 Claims, 1 Drawing Sheet

HIGH EFFICIENCY METHOD FOR ISOLATING TARGET SUBSTANCES USING A MULTISAMPLE SEPARATION DEVICE

CROSS REFERENCE TO RELATED APPLICATION

Reference is made to commonly assigned, concurrently filed applications Ser. No. 08/308,561, (WO 96/09550) entitled "Multisample Magnetic Separation Device", (WO 96/09313), entitled "Methods for Creating Agglomerates From Colloidal Particles" which applications are incorporated by reference herein in their entirety.

TECHNICAL FIELD

The present invention relates to methods or processes for separating or isolating target substances from other media. This invention is particularly applicable where small amounts of starting material(s) are to be processed. More specifically, the present invention relates to methods of separating or isolating a target substance or substances, or a complex from other media where a multisample, preferably magnetic, separation device is utilized. Yet more specifically, this invention relates to highly efficient methods for separating a biological target substance or substances from other media where interfering species such as biological debris has a tendency to interfere with biospecific affinity reaction complex formation during the isolation or separation process.

BACKGROUND OF THE INVENTION

Laboratory and clinical procedures involving biospecific affinity procedures have dramatically affected health care and biological research. Such procedures, which are sometimes referred to as biospecific affinity reactions, are commonly employed in testing biological samples, such as blood or urine, for the identification, quantification, or both of a wide range of target substances. Biospecific affinity reactions have been used, for example, to identify particular chemical substances which have been correlated or associated with disease conditions. Biological entities such as proteins, biomolecules, nucleic acid sequences, e.g., mRNA, and the like, are preferred "target substances" or "target particles" as those terms are used herein.

Various methods are available for identifying the presence or quantity of the above-mentioned target substances in a given medium or environment based upon formation of a complex or a binding reaction between the target substance, i.e., a ligand of interest, and a specific binding partner. The binding partner preferentially binds to the ligand and not to other constituents which may be present in the sample. In each instance, the occurrence or degree of target substance/binding partner complex formation is determinable.

Assays typically used in the art include immunoassays, hybridization assays, and protein-ligand assays. Immunoassays are based upon the specificity of an antibody for an antigen. Hybridization assays are based upon the specificity of complementary nucleic acid sequences, i.e., on the hybridization of nucleic acid probes, with target nucleic acids. Protein-ligand assays depend upon the affinity of a binding site on a protein for a specific ligand, e.g., streptavidin for biotin.

In each assay type, quantitation of the target substance requires a physical separation of bound from free unlabeled ligand or receptor.

In one approach, physical separation of bound from free ligand or receptor may be accomplished gravitationally, e.g., by settling, or, alternatively, by centrifugation, of small diameter particles or beads coupled to the target substance. If desired, such particles or beads may be or can be made magnetic to facilitate the bound/free separation step. Magnetic particles are well known in the art, as is their use in immune and other bio-specific affinity reactions. See, for example, U.S. Pat. No. 4,554,088 and *Immunoassays for Clinical Chemistry*, pp. 147–162, Hunter et al., eds., Churchill Livingston, Edinborough (1983). Generally, any material which facilitates magnetic separation may be employed for this purpose.

Small diameter or small dimensioned magnetic particles have proven to be quite useful in analyses involving biospecific affinity reactions, as they can be conveniently coated with biofunctional molecules, e.g., proteins, which have a binding site for a specific ligand and provide favorable reaction kinetics. Magnetic particles ranging in longest dimension from 3 nm to many microns (and larger) have been described in the patent literature, including, by way of example and not by way of limitation, U.S. Pat. Nos. 3,970,518; 4,018,886; 4,230,685; 4,267,234; 4,452,773; 4,554,088; 4,659,678; 4,978,610; and 5,200,084.

Smaller sized magnetic particles, such as those mentioned above, generally fall into two broad categories. The first category includes particles that are permanently magnetized; and the second comprises particles that become magnetic only when subjected to a magnetic field. Permanently magnetized particles are often referred to as "ferromagnetic". The second class of particles are generally referred to as paramagnetic. For purposes of this application, both classes of particles are collectively referred to herein as "magnetically responsive" particles.

The type of magnetic separation device used for separating target substance-bearing particles from test media will depend on the chemical nature and the particle size of the magnetic particle utilized. Micron-sized paramagnetic particles are readily removed from surrounding media, e.g., a solution, by means of commercially available magnetic separation devices, employing relatively inexpensive permanent magnets. Examples of such magnetic separators are the MAIA Magnetic Separator manufactured by Serono Diagnostics, Norwell, Mass., U.S.A., the DYNAL MPC-1 manufactured by DYNAL, Inc., Great Neck, N.Y., U.S.A., and the BioMag Separator, manufactured by Advanced Magnetics, Inc., Cambridge, Mass., U.S.A. A similar magnetic separator, manufactured by Ciba-Corning Medical Diagnostics, Wampole, Mass., U.S.A., is provided with rows of bar magnets arranged in parallel and located at the base of the separator. The Ciba-Corning device accommodates 60 test tubes, with the closed end of each tube fitting into a recess between two of the bar magnets.

For separation of particles of smaller size, e.g., colloidal dimension and smaller, higher field strength, e.g., higher gradient field separators, may be used. The present invention can be used in the separation of target particles from a medium including such particles, regardless of particle size. The present invention also is applicable to separate target particle/ligand complexes from a medium where the target particle/ligand complex is removable from the medium by techniques other than magnetic. In essence, this invention can be used in any circumstance where a complex is created in a medium for the purpose of isolation or identification and there are substances or chemical species present in the medium which tend to interfere with the formation of the ligand/receptor complex or target particle/binding agent complex or which tend to promote complex breakdown.

In a broader sense, aspects of this invention are applicable to any situation where a suspension or a solution of a target material is to be physically separated from an interfering substance or substances which can be collected or localized, e.g., by centrifugation. This invention provides the means by which the step of separating a target material from an interfering substance, e.g., by transfer of one away from the other via pipette or other means, can be completely avoided.

The concomitant of this invention is that where interfering substances can be localized, e.g., by centrifugation, subsequent processing of the target particles or target substance solution/suspension can be accomplished in the same centrifuge sample well.

This invention results in savings of time, e.g., by eliminating transfer steps, and minimizes the quantity of expensive or potentially scarce or difficult to obtain starting materials. This invention reduces the likelihood of sample cross contamination, reduces user error, provides greater reproductability of results, and provides a significant reduction in the use of disposable pieces, e.g., micropipette tips and tubes. Reproducibility can be obtained even though very small samples of biological interest, e.g., 20 mg or less, are used. Where, for example, analysis of tissue or organ samples obtained in a biopsy, is contemplated, the ability to do reproducible, qualitative or quantitative analyses on small, biological samples can be very important to reduce patient trauma. Lastly, as is described below, this invention is particularly applicable to automated processing systems and can be used to enhance their efficiency.

This invention solves a particular problem which sometimes occurs during the formation of complexes such as receptor/ligand complexes or in the separation of such receptor/ligand complexes from the medium in which they are dispersed. Specifically, it was found that, in the isolation of mRNA, after cell disruption or homogenation, dilution and centrifugation to generate cleared cell lysates, the precipitated proteins and cellular debris in the end of the centrifuge tube (usually in the form of a pellet) would interfere with complex formation between magnetic streptavidin particles and biotinylated oligo (dT):mRNA complexes. The specific interference caused by the unwanted proteins and cellular debris was interference in the release of mRNA from magnetic streptavidin particles upon addition of distilled water to collected streptavidin particles having biotinylated oligo (dT):mRNA complexes thereon.

One approach to this problem was simply to transfer cleared lysate from the centrifuge tube into a sterile tube and to perform the mRNA purification procedure, e.g., by formation of a magnetic complex, in the absence of cell and tissue debris. This approach generally involved pipetting of cleared lysate from one tube to another. Where a limited number of samples was utilized, e.g., five or less, physical transference of cleared lysate by pipetting was and is an acceptable procedure.

However, in the context of, for example, high throughput, multiple-well (e.g., five or more) plate magnetic isolation devices, performing a physical transfer step, such as pipetting, is time consuming, prone to error, subject to sample contamination or sample loss, generates large quantities of unwanted disposables, e.g., plastic pipette tubes, and permits the undesirable transfer of interfering substances.

The present invention therefore is applicable in the circumstance where target substances are to be isolated from a medium using multiple well plates and interference with complex formation or isolation, as discussed above, is experienced. The invention provides enhanced reproducibility, even where small or very small samples are involved. A specific, preferred, multiple well plate used in a magnetic separation process is that described in applicants' commonly assigned and concurrently filed patent application referred to above.

SUMMARY OF THE INVENTION

Briefly, in one aspect, the present invention is a method for isolating or detecting (or both) a target substance of biological interest from interfering biological debris, especially where a multi-well separation device is employed. Biological target substances in the present invention are collected by the formation of a complex with a second substance, the complex having properties which permit it to be separated from the medium in which it is dispersed.

In a preferred practice of the present invention, the target substance interacts with a magnetically responsive second particle to form a complex which may be separated from the biologic medium by application of magnetic separation techniques. While this invention is specifically described with respect to application of magnetic separation techniques, other techniques such as application of electrical energy, e.g., repulsion/attraction, irradiation, or chemical interaction and the like, may be employed.

As used herein, the term "target substance" or "target particle" refers to any member of a specific binding pair, i.e., a pair of substances or a substance and a structure exhibiting a mutual affinity of interaction and includes such things as cell components, biospecific ligands and receptors.

"Ligand" is used herein to refer to substances, such as biotin, antigens, haptens, proteins, nucleic acids and various cell-associated structures, having at least one characteristic determinant or epitope, which are capable of being biospecifically recognized by and bound to a receptor.

"Receptor" is used herein to refer to any substance or group of substances having a biospecific binding affinity for a given ligand, to the substantial exclusion of other substances. Among the receptors determinable via biospecific affinity reactions are biotin-binding proteins (e.g., avidin and streptavidin), antibodies (both polyclonal and monoclonal), antibody fragments, enzymes, proteins, nucleic acids, and the like. The determination of any member of a biospecific binding pair is dependent upon its selective interaction with the other member of the pair.

As used herein, the term "magnetic" is meant to refer to permanently and temporarily magnetic materials, and to magnetically responsive materials, i.e., materials capable of being magnetized in the presence of a magnetic field but which are not magnetic in the absence of such a field, such as paramagnetic materials.

DETAILED DESCRIPTION

Figure 1:
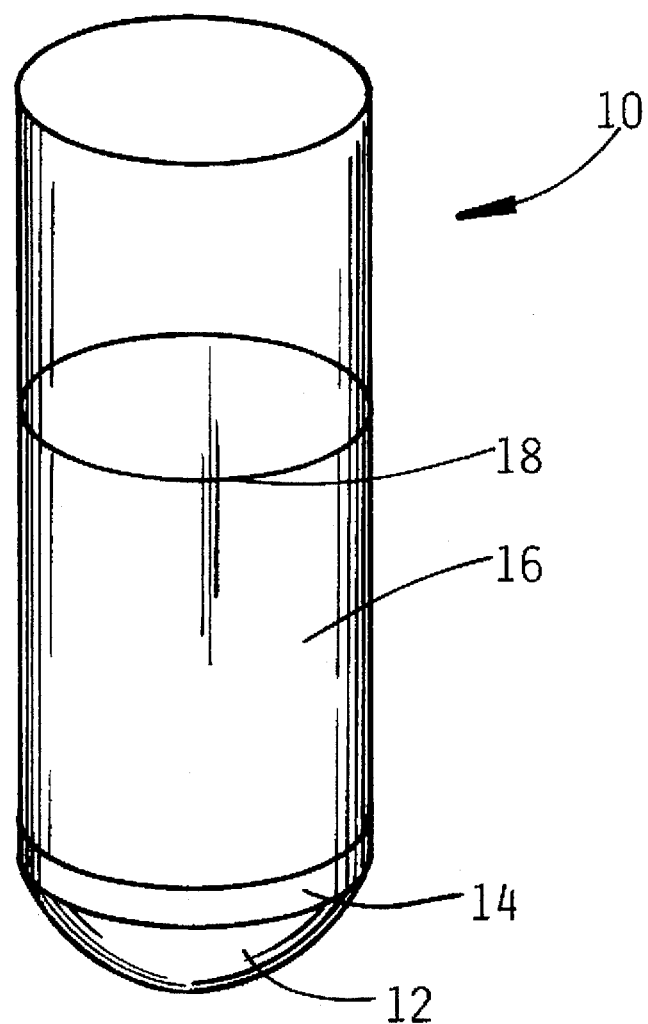
FIG. 1 is a perspective schematic illustration of a microcentrifuge tube or well utilizing the present invention.

The present invention provides an improved method for separating a material of biological interest suspended, dissolved, or otherwise dispersed in a medium from interfering biological materials. This invention is preferably utilized with magnetic separation devices for separation of magnetic particles from nonmagnetic media utilizing a multi-well or multi-titer separation device. While a 96-well separation device is disclosed, a separator with five or more wells can be used more effectively in a practice of this invention. The present invention is particularly well-suited for use in separating biological substances of interest in various laboratory and clinical procedures involving biospecific affinity reactions. Accordingly, the present invention will now be described in detail with respect to such endeavors. However, those skilled in the art will appreciate that such a description of the invention is meant to be exemplary only and should not be viewed as limitative of the full scope thereof.

A preferred method in accordance with the present invention utilizes particles which are magnetically responsive and which comprise a receptor capable of binding the substance of interest in the test sample. After the receptor binds the target substance, a magnetic separator is used to remove the magnetic particles bound to the substance of interest from the test medium.

Biospecific affinity reactions may be employed in testing biological samples for the determination of a wide range of target substances. Representative target substances include cells, cell components, cell subpopulations (both eucaryotic and procaryotic), bacteria, parasites, antigens, proteins, specific antibodies, specific biological factors, such as vitamins, viruses and specific nucleic acid sequences, e.g., mRNA. Thus, the magnetic separation aspect of this invention has application in cell separations for the analysis or isolation of cells including, by way of example: T-cells from a T-cell lymphoma cell line; B-cells from a B-cell lymphoma cell line; CD4 positive cells from leukocytes; and lymphocytes from leukocytes.

The methods in accordance with the invention may also be used for immunospecific isolation of monocytes, granulocytes and other cell types; removal of rare cells; depletion of natural killer cells; determination of reticulocytes; and assays for neutrophil function, e.g., for determining changes in membrane potential, performing oxidative burst analysis, phagocytosis assays and opsonization studies.

Similarly, the magnetic separation aspect of the present method may be used in separation of pathogens, including but not limited to the separation of various bacteria and parasites from fecal matter, urine, sludges, slurries and water (e.g., ground water or streams). The present invention may also be used in separating various bacteria in food products (liquids to solids), sputum, blood, urine, body fluids, and homogenates of body fluids.

Magnetic particles may comprise paramagnetic materials such as, for example, metals (e.g., iron, nickel or cobalt), metal alloys (e.g., magnetic alloys of aluminum, nickel and cobalt) and metal oxides (e.g., $Fe_3O_4$ or $Fe_2O_3$). The preferred material is the paramagnetic ferric oxide.

The paramagnetic particles may be provided with a nonmagnetic polymeric matrix or coating. Suitable materials are composed of a crystalline core of magnetically responsive material surrounded by molecules which may be physically absorbed or covalently attached to the magnetic core. For example, preferred are particles of an iron oxide core surrounded by receptor molecules or molecular probes depending on the type of ligand to be separated.

The preferred magnetic particles for use in carrying out this invention are particles having a size in the range of about 500 nm to about 2 µm, i.e., noncolloidal particles that are subject to settling if undisturbed. Magnetic particles having the above-described properties are, for example, streptavidin-coated iron oxide paramagnetic particles which are commercially available from Promega Corporation, Madison, Wis., U.S.A. under the trade designation Streptavidin MagneSphere® Paramagnetic Particles. Streptavidin MagneSphere® Paramagnetic Particles (SA-PMP's) are used in the magnetic separation or purification of various biotinylated molecules. Conversely, streptavidin may be separately purchased, e.g., from Promega Corporation, and coated upon paramagnetic particles, e.g., those particles available from Advanced Magnetics, Cambridge, Mass., U.S.A. In the context of this invention, mRNA may be isolated/separated.

For cell separations, the test medium is typically prepared from body fluids or tissues, such as blood, urine, sputum, secretions, or tissue samples. If magnetic separation is to be utilized, it is preferable to add the magnetic particles to the test medium in a buffer solution. A preferred buffer solution for, e.g., RNA isolations, is PolyATtract wash solution commercially available from Promega Corporation, Madison, Wis., U.S.A. The wash solution should be isotonic, with a pH of about 7 and preferably contains 0.5× SSC 10 µg/ml bovine serum albumin (BSA). The target substance may be added to the test medium before, after or simultaneously with introduction of the blocking particles. However, for hybridization assays, e.g., mRNA purification, it has been found that the magnetic particles are suitably added to the target substance after the hybridization reaction occurs and after blocking or masking of the cellular debris, according to this invention. The test medium is usually incubated to promote binding between the receptor and any ligand of interest present therein. Incubation is typically conducted at room temperature, at a temperature slightly above the freezing point of the test medium (i.e., 4° C.) or even at elevated temperatures (e.g., 70° C.). The period of incubation is normally of short duration (i.e., about 1 to about 15 minutes). The test medium may be agitated or stirred during the incubation period to facilitate contact between receptor and ligand.

After binding of the receptor to the substance of interest is allowed to occur, magnetic separation of the magnetic particles from the test medium is performed in accordance with the above-cited co-pending application.

One of the advantages of the present invention is that, in one practice, a target substance such as mRNA, can be hybridized in solution to the biotinylated oligo (dT) probe, rather than to a probe directly coupled to paramagnetic particles. This permits the user to achieve the combined speed and efficiency of solution hybridization with the convenience and speed of magnetic separation. The Streptavidin Paramagnetic Particles, SA-PMP (especially the MagneSphere® particles available from Promega Corporation), exhibit a high binding capacity for biotinylated oligonucleotides and very low nonspecific binding of nucleic acids. While the binding capacity of the SA-PMP varies with the specific oligonucleotide probe used for biotinylated oligo (dT), the binding capacity is approximately 1 nmol of free probe captured per mg of SA-PMPs.

The method of this invention utilizes "blocking" or "masking" particles to reduce or eliminate interference in the formation of magnetic complexes by cellular debris and precipitated proteins. The preferred blocking particles used in this invention are carboxylated polystyrene latex (especially fluorescent labeled yellow versions), 0.043 µm, commercially available from Magsphere, Inc. of Pasadena, Calif., U.S.A. The blocking particles are added in sufficient quantity so as to cover, layer over, encase, encapsulate, or create a barrier over cellular debris which tends to be located in the extreme end of a centrifuge tube following centrifugation. The blocking particles generally are used in the isolation process between the steps of homogenation of the biological source containing the target particles and centrifugation of the homogenized medium to generate cleared lysate containing target particles. In other words, blocking particles are utilized in the isolation method after hybridization of mRNA and biotinylated oligo (dT) probe and before a biospecific affinity reaction is run. In the above-described, preferred description of the invention, after the above steps, SA-PMPs are added to the cleared lysate to generate a magnetically-responsive complex with the mRNA target particles which can then be magnetically isolated.

The use of multi-well, magnetic separation techniques suggests several of the criteria which must be considered when selecting blocking or masking particles for utilization of this invention where other, non-magnetic, separation techniques are to be employed.

Of primary importance, the blocking or masking particles chosen should not, themselves, interfere with intended complex formation. In the context of the preferred practice of this invention, the carboxylated 0.04 µm polystyrene particles selected do not interfere with complex formation between mRNA target particles and paramagnetic streptavidin particles. If other target particle/ligand interactions, e.g., chemical bonding, hydrogen bonding, electro-repulsion, irradiation, electro-attraction, physical restraint (e.g., molecular sieve), are used to create complexes, the blocking particles selected must not interfere with that complex formation.

Also to be considered is that the blocking or masking particles chosen should be of a size, density, chemical composition, or surface configuration or chemical characteristics so that they will agglommerate, accumulate or otherwise associate to form a protective layer or coat over unwanted, interfering debris in a centrifugation step. In this manner, interference with complex formation is minimized or eliminated because a physical separator, or a barrier layer between the debris and cleared lysate or medium containing target particles is provided. The preferred blocking particles, under the conditions described below, have been found to increase substantially in apparent volume. This feature tends to make them particularly attractive for utilization in the present invention.

Further, the masking or blocking particles should interact with each other in a compacting, aggregating, or associating manner, e.g., in response to the gravitational forces generated during centrifugation, to create a layer, encasing, or coating which is substantially impermeable to the contained or "trapped" interfering debris. It is the trapping or localization of potentially interfering debris by utilization of blocking particles which provides the many advantages of this invention discussed above.

The utilization of masking or blocking particles provides a further unexpected advantage which is particularly applicable to multi-well separation systems, especially if automated systems are contemplated. The quantity of blocking particles can be used to adjust the volume relationship between cleared lysate and debris generated in centrifugation. Since the particles occupy part of the volume, e.g., of a Microtiter™ well (Microtiter is a trademark of Dynal Corporation, Lake Sucess, N.Y., U.S.A), their quantity may be adjusted to control precisely liquid levels within each well. In other words, liquid levels within a well can be controlled without the need to change the quantity of potentially scarce biological starting material containing target particles. Where magnetic pin separators which are dipped into an array of wells are used (e.g., those described in the concurrently filed application incorporated by reference above), the ability to control liquid levels within the system, in a cost-effective manner, may be very useful.

One skilled in this art will be able to select appropriate blocking particles or materials in light of the above teaching and of the isolation process employed. Substantially chemically inert, non-magnetic, colloidal, polyolefinic particles of the above-discussed size to work well if magnetic separation is employed. Other classes of particles could include ceramic materials, molecular sieves, carbon particles, electrically conductive or non-conductive particles of all chemistries, polymeric or polymerizable particles of other types, latexes, diatomaceous earth, non-soluble powders, glycerol, polyethylene glycol polyethers (PEG), acrylamide particles, agaroses, and the like.

The present invention, when utilized with the separation apparatus of the concurrently-filed, co-pending application, provides the first method for combined mRNA purification and conversion to first strand cDNA, optimized for the small amounts of multiple samples needed for RT-PCR. All methods for isolation of intact RNA require that four important steps be performed: 1) effective disruption of cells or tissues, 2) denaturation of nucleoprotein complexes, 3) inactivation of endogenous ribonuclease (RNase) activity, and 4) purification of RNA away from contaminating DNA and protein.

The method incorporates significant improvements for the rapid and uniform isolation of mRNA from small amounts of tissue ($\leq 2.5$ mg) or cultured cells ($\leq 10^5$ cells). Biological samples are prepared in guanidine thiocyanate (GTC) extraction buffer and then transferred to a separation chamber comprising, e.g., 96 well plates. Cell lysates prepared in this buffer can be stored indefinitely at −70° C. because GTC and β-mercaptoethanol (BME) tend to inactivate ribonucleases. GTC, in association with sodium dodecyl sulfate (SDS), a detergent, also acts to disrupt nucleoprotein complexes, allowing RNA to be released into solution and isolated free of protein. Furthermore, dilution of the highly concentrated cell extracts in a salt buffer effectively precipitates cellular proteins. To prevent cellular debris and precipitated proteins from interfering with the mRNA purification procedure, the lysates are cleared by centrifugation in the presence of bovine serum albumin (BSA) polystyrene blocking particles. The particles form a tight pellet over the cellular debris, effectively forming a barrier between the cleared lysate and the cellular debris. The final GTC concentration allows for effective hybridization between the poly(A)+ sequence of most eukaryotic mRNA species and the synthetic Biotinylated Oligo (dT) Probe, yet maintains complete inhibition of cellular RNases.

The biotinylated Oligo (dT):mRNA hybrids are captured by adding streptavidin-coated paramagnetic particles (SA-PMPs) and then immobilizing them on a 96 pin array. The mRNA complexes immobilized on the 96 pin array are then bulk-washed at high stringency to remove any residual contaminating proteins, DNA, and non-polyadenylated RNA and then transferred to a fresh 96 well plate containing Nuclease-Free Water to rupture the dT:RA bonds, thereby releasing the purified mRNA into solution.

The present invention was developed in view of, and optimized for, mRNA isolation from tissues with a broad spectrum of mRNA expression levels. To ensure quantitative capture from tissues high in mRNA, utilization of an excess of mRNA binding capacity is recommended. Further, to maintain sufficient molar concentrations of the biotinylated oligo(dT) and the mRNA for hybridization, the volumes of the extraction and hybridization buffers (described below) must be kept to a minimum. Generally this means the maximum sample concentration of 2.5 mg of tissue or $10^5$ cells per 20 µl of GTC Extraction Buffer should not be exceeded.

Exceeding the maximum recommended sample concentration tends to generate increased lysate viscosity leading to irreversible clumping of the particles during magnetic capture. This results in lower RNA yields. If more than 2.5 mg of tissue or $10^5$ cells must be processed, the amount of extraction buffer added during the homogenization step should be increased to maintain the 2.5 mg:20 µl ratio. mRNA is stable indefinitely when homogenized in GTC Extraction Buffer and stored at −70° C., allowing advance preparation of samples if necessary. If greater amounts of cDNA are needed, then multiple 20 µl aliquots from the same lysates may be prepared and the resulting cDNA pooled after completion of the procedure.

Reverse transcription of RNA followed by PCR amplification (RT-PCR) is an extraordinarily sensitive method to detect as few as 1 to 100 copies of a specific RNA segment. RT-PCR offers the opportunity to probe specifically for gene products of many different genes from minute amounts of starting material. The present invention increases the overall efficiency of the RT-PCR procedure thereby making it even more sensitive. Transcription itself is known to be approximately 10%–15% efficient. Experiments can be designed to compare gene expression between control and experimental groups, or within a single individual or group at different times relating to an intervention. In addition, recent techniques allow the quantitation of specific messages using reverse transcription of the RNA followed by PCR.

The present method can be used with a wide variety of samples, including nerve, skin, liver and brain tissue and cultured fibroblasts, lymphocytes, macrophages and endothelial cells. Caution must be exercised when processing any human samples or infectious materials. Gloves must be worn and precautions taken to contain aerosols generated during homogenization. All surfaces and instruments must be disinfected after use.

In accordance with accepted laboratory practice, sterile technique should be used throughout. Nucleic acid carryover and cross-contamination also must be vigorously avoided if sensitivity is to be maintained.

The following examples further describe in detail the manner and process of making and using the present invention. The examples are to be considered as illustrative but not as limiting of this invention. All temperatures given in the examples are in degrees Celsius, unless otherwise indicated.

EXAMPLE 1

As is noted above, the present invention is particularly applicable to situations where a multiple well magnetic separation device is employed. For example, mRNA can be isolated in parallel from 48, 96 (or more) tissue or cell samples and converted into first strand cDNA in approximately 2.5 hours (excluding sample preparation). A separator having a well array of five or more wells is generally what is intended by the terminology of "multiple well" as used herein. Polymerase chain reaction (PCR) processes may be performed on the cDNA in the same time period with no further sample preparation.

In this example of the present invention, high capacity streptavidin paramagnetic particles (SA-PMP), biotinylated oligo (dT), a 96 pin magnetic separator, and non-magnetic blocking particles were employed. First strand cDNA then was synthesized by the simple addition of M-MLV (H-) Reverse Transcriptase reaction mixture directly to the multiple well plate. The cDNA thereby generated was generally more stable than RNA and can be directly stored in the 96 well plate. Because an entire mRNA population is represented in each sample, the cDNA can be probed for multiple genes from the same tissue or cell sample. Further, by utilization of a multiple well microtiter plate, samples may be processed in parallel, thereby facilitating direct comparison between identical samples exposed to differing process conditions.

A typical kit for practicing the present invention with, e.g., a 96 well plate magnetic separation device, has the following components:

| | |
|---|---|
| 30,000 u | M-MLV (H−) Reverse Transcriptase, 200 u/µl |
| 3 ml | RT 9600 Gold Buffer |
| 50 µl | dNTP Mix, 10 mM of each dNTP |
| 175 µg | Oligo(dT)$_{15}$ Primer, 500 µg/ml |
| 10,000 u | rRNasin ® Ribonuclease Inhibitor, 40 u/µl |

The components listed above are sometimes referred to as the cDNA Master Mix.

| | |
|---|---|
| 80 µl | Mouse Liver Lysate, 125 µg/µl |
| 120 ml | PolyATtract ® GTC Extraction Buffer |
| 15 ml | Hybridization Buffer with Biotinylated Oligo(dT) Probe |
| 15 ml | Blocking Particles, 0.04 micron carboxylated, yellow dyed, polystyrene particles |
| 20 ml | Streptavidin MagneSphere ® Paramagnetic Particles available from Promega Corporation |
| 150 ml | PolyATtract Wash Solution [SSC, 0.5X Solution] |
| 25 ml | Nuclease-Free Water |
| 6 | 96 Well V-Bottom Plates |
| 6 | 48 Well GeNunc ™ Modules |
| 2 | GeNunc ™ Frames |
| 2 | GeNunc ™ Frame Supports |
| 3 | Plate Sealers |
| 24 | Strip-Ease ® PCR Tube Caps |

The above materials are available from Promega Corporation, Madison, Wis., U.S.A.

GeNunc frames and frame supports are commercially available from the Nunc Inc. located in Naperville, Ill., U.S.A. Strip-ease PCR tube caps are commercially available from the Robbins Scientific Corporation located in Sunnyvale, Calif., U.S.A.

Utilizing the above components, the following steps were performed:

1. GTC extraction buffer was added to tissue, e.g., mouse liver lysate, at a ratio of 20 gl per 2.5 mg (or less) of tissue or 20 gl per $1\times10^5$ (or less) tissue culture cells.

2. The mixture of step 1 was homogenized using a Polytron Homogenizer, Brinkmann Instruments, Westbury, N.Y.

3. 20 gl of each sample was transferred to a well. For example, 96 such 20 gl samples are transferred in a typical application of the present invention.

4. 40 gl of prewarmed (e.g., to 70° C.) hybridization buffer comprising biotinylated oligo (dT) probe was added per well and incubated at room temperature for five minutes.

5. 35 µl of blocking or masking particles were added per well, the plate was sealed, and centrifuged for ten minutes at room temperature. The centrifugation step should be accomplished at approximately 1,700×g. This step traps precipitated proteins and insoluble cell material underneath the pellet of blocking particles.

At this point, a typical sample will contain (proceeding from the bottom of the centrifuge tube) a pellet or collection of cell debris covered by a pellet or layer of masking or blocking particles. Lastly, above the pellet of blocking particles is cleared cell lysate comprising mRNA target particles dispersed in the medium, i.e., buffer.

Referring now to FIG. 1, shown in expanded perspective view, is one titer well 10 of what would be an extended array, e.g., 96, of such wells. Well 10 appears as it would subsequent to centrifugation step 5 above. Within well 10 is cell debris and precipitated proteins in the form of a pellet 12. Covering pellet 12 is a layer of blocking particles 14. Over layer 14 is cleared cell lysate 16. Cleared cell lysate 16 contains mRNA which, in further processing, will be separated from the buffer medium. Blocking particle layer 14 comprises 0.04 micron carboxylated polystyrene particles (i.e., a latex). A sufficient quantity of such particles is added to create layer 14 which separates cleared cell lysate 16 from cell debris 12. Prior to the present invention, in order to prevent interference between cell debris 12 and a target substance in lysate 16, it would have been necessary for cleared lysate 16 to be removed from cell 10 to a clean reaction chamber. It is elimination of this procedure which is one of the primary advantages of the present invention. Lysate 16 protected from debris 12 by layer 14 may now be exposed to subsequent processing steps, e.g., magnetic separation, resulting in the collection of target substance, e.g., mRNA, therefrom.

Further, the width of layer 14 may be adjusted by changing the quantity of particles 14, thereby changing liquid level 18 (assuming a fixed quantity of liquid). The ability to adjust liquid level 18 by adjusting the quantity of blocking particles 14 is potentially a useful tool for automating isolation/transcription/amplification processes.

6. 60 µl of SA-PMPs were added to each well and incubated at room temperature for two minutes.

EXAMPLE 2

The pin array of a magnetic separator described in the above-cited concurrently filed application was treated in 1N sodium hydroxide for one minute before use. The pins were then rinsed with sterile $H_2O$.

EXAMPLE 3 mRNA Purification

The array of wells generated in Example 1 was then placed into the base of a multiple pin/magnetic separator as described in the above-referenced, concurrently filed application. The hinges of the pin plate were positioned in the hinge channels of the base and the pin plate was carefully lowered into the Microtiter™ plate. The external magnet pack was then placed on the pin plate, contacting the pin ends and the admixtures were incubated until the magnetic particles were cleared from the lysate, typically about 90 sec.

The pin plate and magnet were then raised to a 45° angle, and the Microtiter plate containing the cell lysates was replaced with a fresh plate containing 165 µl of 0.5× SSC 10 µg/ml BSA in each well. The magnet pack was removed and the attached particles were released to wash by raising and lowering the pin plate. The particles were recaptured by placing the magnet pack in contact with the pins. The release and recapture steps were repeated for a total of two washes of the SA-PMP complexes. The rinse Microtiter™ plate was then removed and replaced with a GeNunc plate containing 20 µl of $dH_2O$ in each well. The pin plate and magnet were lowered so that the pins were immersed. The magnet was removed and the particles were released in nuclease free water and recaptured, releasing the mRNA into solution.

After 1 min, the magnet was returned to position atop the pin plate and collected the particles on the pins, typically about 90 sec. The remaining water medium contained purified mRNA.

EXAMPLE 4

The purified isolated mRNA generated in Example 3 was used to synthesize cDNA by adding 10 µl Reverse Transcriptase Master Mix, components commercially available from Promega Corporation, Madison, Wis., U.S.A., to the wells and incubating the mixture at 37° C. for 30 minutes followed by heat inactivation for 5 minutes at 95° C.

In summary, the present invention provides a simple, cost-effective, efficient, high throughput method for effective separation of multiple small samples and facilitating processing steps, especially the magnetic particle-ligand complex.

EXAMPLE 5

In this example, carboxylated polystyrene latex blocking particles colored with fluorescent yellow dye were used. Such particles are commercially available from Magsphere Inc., Pasadena, Calif., U.S.A. The particles had a size of about 0.043 µm and comprise a yellow color water-based latex with about 10% dyed polymer particles in water medium on a weight per unit volume basis. The yellow color is used primarily to identify the presence of the particles during the processing steps.

Aggressive centrifugation of the water-based latex blocking particles, substantially as purchased, produced no precipitate or agglomerate. Under observation in a micro fluoroscope, the substantially independent particles appear to float in the aqueous medium, apparently being subject to Brownian movement.

The blocking particles have been found to create agglomerates, aggregates, clusters, or "flocs" which are capable of centrifugation, as follows:

Two ml of stock carboxylated polystyrene latex particles are placed in a centrifuge tube. Six ml of GTC Extraction Buffer was added to the tube and next, 12 ml of dilution buffer which has been heated to 70 degrees C. GTC extraction buffer is commercially available from Promega Corporation under the trade name PolyATtract® and comprises: 4M guanidine thiocyanate, 25 mM sodium citrate, and 2% β-mercaptoethanol. The dilution buffer comprises 0.01M Tris-HCl, pH 7.5, 6×SSC, 0.24% sodium dodecyl sulfate (SDS), 0.001M EDTA, and 1% beta-mercaptoethanol (BME). The materials are mixed and centrifuged at 1,700×G for ten minutes. Under fluorescent microscopy, the resulting agglomerates are sheetlike. The particles did not evidence Brownian motion. Even though only about 2 ml of particles was employed in the process, their packed volume after agglomeration and centrifugation is approximately 5 ml.

EXAMPLE 6

In this example, spherically-shaped agglomerates or coagulants were created.

GTC extraction buffer and dilution buffer, in the amounts indicated in Example 5, were first mixed together. Two ml of stock masking particles were then added to the premixed buffers. After mixing and centrifuging the mixture, as described in Example 5, the agglomerates appeared to be substantially spherical under fluorescence microscopy.

EXAMPLE 7

Individual mixtures of 2 ml of stock particles and the quantities of Tris, SDS solution, 6×SSC solution and EDTA solution indicated in Example 5 were prepared. After mixing and centrifugation under the conditions indicated in Example 5, no agglomerates or precipitate was generated. From this it was concluded that all the above buffer components had to be present for the desired agglomeration reaction to occur.

EXAMPLE 8

This example involves the collection by agglomeration of colloidal-dimension magnetic particles that could not otherwise be collected using conventional, low magnetic strength separation techniques.

In this example, magnetically responsive particles of less than one micron major diameter would be used. Particles to which this aspect of the invention applies are described in U.S. Pat. No. 5,200,084 to Liberti et al., at column 2 lines 65–68, and are apparently discussed in U.S. patent application Ser. No. 389,697 filed Aug. 4, 1989, which application is referred to at column 3, lines 35, 41 of the Liberti et al. '084 patent. Both the above excerpts from the '084 Liberti et al. patent, and the references cited in those excerpts, are incorporated by reference herein. Magnetically responsive particles of that dimension would be of true colloidal dimension and would not be removed from solution or suspension by conventional centrifugation. In this example, submicron magnetically responsive particles would be mixed with GTC buffer, and dilution buffer in ratios substantially as disclosed in Example 5. Agglomeration is permitted to occur generating particles of a supra micron (i.e., above 1 micron), non-colloidal major dimension. These substantially larger particles may be separated from the medium in which they were dispersed by centrifugation or by application of relatively low magnetic fields.

EXAMPLE 9

The compositions of buffers and solutions referred to herein are as follows:

---
1X PBS, pH 7.4:

0.2 g/L KCl
8.0 g/L NaCL
0.2 g/L $KH_2PO_4$
1.15 g/L $Na_2HPO_4$

PolyATtract® GTC Extraction Buffer:

4M guanidine thiocyanate
25 mM sodium citrate
2% β-mercaptoethanol

PolyATtract® Wash Solution:

7.5 mM sodium citrate
75 mM NaCl
10 µg/ml bovine serum albumin (BSA)

Hybridization Buffer with Biotinylated Oligo(dT) Probe:

10 mM Tris-HCl, pH 7.1
90 mM sodium citrate
900 mM NaCl
1 mM EDTA
0.25% SDS
1% β-mercaptoethanol
75 nM Biotinylated Oligo(dT) Probe

RT 9600 Gold Buffer:

40 mM Tris-HCl, pH 8.3
202 mM KCl
6 mM $MgCl_2$
8 mM DTT
2.7% yellow dye

20 X SSC:

3.0M sodium chloride
0.3M sodium citrate

---
pH adjusted to 7.0 with NaOH.

EXAMPLE 10

Messenger RNA, purified from 2-fold serially diluted Mouse Liver Lysate, as described above, was reverse transcribed and amplified by PCR for detection of a rare cytokine mRNA, IL-1β. Amplification was performed using Taq DNA Polymerase from Boehringer Mannheim according to their specifications for PCR conditions. Five microliters of each 300 µl cDNA sample were amplified in a 50 µl PCR reaction containing 1 µM of each primer. Twenty microliters of each PCR reaction were analyzed on a 2% agarose gel and stained with ethidium bromide. Each 20 µl sample corresponds to $\frac{1}{15}$ of the original tissue or cell sample. RT-PCR product was faintly detected at the lowest level of starting material.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is as follows:

1. A method for isolating a biological target substance from interfering biological debris in a medium utilizing a multi-well separation device wherein the target substance interacts with a second species to form a complex, the second species having a receptor capable of binding the target substance, said complex being collectable by application of an external force to the medium; the method comprising the steps of:

providing a mixture comprising the target substance and debris in the medium;

distributing the mixture to a separation device comprising a multiple well array;

precipitating the biological debris in the wells;

adding non-magnetic masking or blocking particles to the wells;

centrifuging the well array to generate multiple individual wells, each of said wells having therein from bottom to top:

biological debris having thereover;
a layer of the non-magnetic particles; and
medium comprising the target particles;

adding the second species to the medium and permitting it to interact with the target substance to generate a complex; and separating the complex from the medium by application of external force.

2. A method for isolating a biological target substance from interfering biological debris utilizing a multi-well separation device wherein the target substance interacts with a Second species of permanently magnetic or magnetically responsive particles to form a complex, the second species having a receptor capable of binding the target substance, said complex being collectable using magnetic separation techniques, the method comprising the steps of:

homogenizing a source of the target substance to provide a mixture of the target substance and debris in a medium;

distributing the mixture to a magnetic separation device comprising an array of wells;

precipitating the biological debris in the wells;

adding non-magnetic masking particles to the wells;

centrifuging the well array to generate multiple individual wells having therein from bottom to top:
 biological debris having thereover;
 a layer of the non-magnetic particles; and
 medium comprising the target particles;

adding the second species to the wells of the well array and permitting it to interact with the target substance to generate a complex comprising the target substance and the second species; and separating the complex from the medium using magnetic separation techniques.

3. A method according to claim 2 wherein the source of the target substance is tissue.

4. A method according to claim 2 wherein the precipitating step is accomplished by adding a dilution/hybridization buffer to the wells.

5. A method according to claim 2 wherein the non-magnetic particle comprises polystyrene.

6. A method according to claim 2 wherein the major dimension of the non-magnetic particles is in the range of 0.03 to 0.05 microns.

7. A method according to claim 2 wherein the debris is cellular debris and protein.

8. A method according to claim 2 wherein the target substance is mRNA.

9. A method according to claim 2 wherein the multiple well magnetic separation device has more than about 5 wells.

10. A method according to claim 2 wherein the magnetic particles are streptavidin paramagnetic particles.

11. A method according to claim 2 wherein the target substance is DNA.

12. A method according to claim 2 wherein the target substance is protein.

13. A method for separating a complex generated via a biospecific affinity reaction wherein said complex is responsive to application of external energy so as to be separable from a medium containing same, the method comprising the steps of:

homogenizing a source of the target substance to provide a mixture of the target substance and the debris in a medium;

distributing the mixture to a separation device comprising a well array;

adding masking or blocking particles to the wells of the array;

centrifuging the well array to generate multiple individual wells having a layer of blocking particles separating biological debris and cleared medium comprising target substance;

creating a biospecific complex by adding a biospecific receptor capable of binding the target substance and permitting the target substance and receptor to interact, the biospecific complex having means by which it can be separated from the medium by application of external force; and separating the biospecific complex from the medium by application of the external force.

14. A method according to claim 13 wherein said external force is magnetic.

15. A method according to claim 13 wherein the target substance is mRNA.

16. A method according to claim 13 which further includes the step of separating the receptor from the target substance to generate isolated target substance.

17. A method according to claim 16 wherein the target substance is mRNA and the isolated mRNA is used for reverse transcription (RT).

18. A method according to claim 17 wherein reverse transcription is followed by PCR amplification.

19. A method according to claim 16 wherein the target substance is cloned.

20. A method according to claim 19 wherein the target substance is DNA.

21. A method according to claim 2, wherein the target is mRNA hybridized to a biotinylated oligo (dT) probe, and wherein the receptor is streptavidin.

22. A method according to claim 8, wherein the receptor is streptavidin coupled to a biotinylated oligo (dT) probe.

23. A method according to claim 15, wherein the receptor is biotinylated oligo (dT), and wherein the means by which the complex can be separated from the medium is by at least one streptavidin coated paramagnetic particle bound to the complex.

* * * * *